United States Patent [19]

Mitariten et al.

[11] Patent Number: 5,457,256
[45] Date of Patent: Oct. 10, 1995

[54] PROCESS FOR SEPARATING DEHYDROGENATION PRODUCTS

[75] Inventors: Michael J. Mitariten, Peekskill; Robert K. Busch, Grand Island, both of N.Y.

[73] Assignee: UOP, Des Plaines, Ill.

[21] Appl. No.: 254,850

[22] Filed: Jun. 6, 1994

[51] Int. Cl.⁶ .............................. C07C 5/327; F25J 3/06
[52] U.S. Cl. .................. 585/655; 62/23; 62/24; 62/27
[58] Field of Search .................. 585/655; 62/23, 62/24, 27

[56] References Cited

U.S. PATENT DOCUMENTS

| | | | |
|---|---|---|---|
| 3,725,246 | 4/1973 | Kmecak et al. | 585/655 |
| 4,381,417 | 4/1983 | Vora et al. | 585/655 |
| 4,381,418 | 4/1983 | Gewartowski | 585/655 |
| 4,430,517 | 2/1984 | Imai et al. | 585/660 |
| 4,469,811 | 9/1984 | Lucien | 502/227 |
| 4,486,547 | 12/1984 | Imai et al. | 502/223 |
| 5,177,293 | 1/1993 | Mitariten et al. | 585/655 |
| 5,227,567 | 7/1993 | Mitariten et al. | 585/661 |

*Primary Examiner*—Sharon A. Gibson
*Assistant Examiner*—Nhat D. Phan
*Attorney, Agent, or Firm*—Thomas K. McBride; John G. Tolomei; Richard P. Silverman

[57] ABSTRACT

A process is disclosed for the catalytic dehydrogenation of $C_3$–$C_4$ hydrocarbons wherein an integrated scheme comprising a cold box unit and a pressure swing adsorption unit is employed to reject methane produced in the dehydrogenation reaction from the hydrogen-rich recycle stream. The process results in a significant improvement in the efficiency of the separation of the reaction by-products and a corresponding increase in the overall feed capacity of the process.

12 Claims, 1 Drawing Sheet

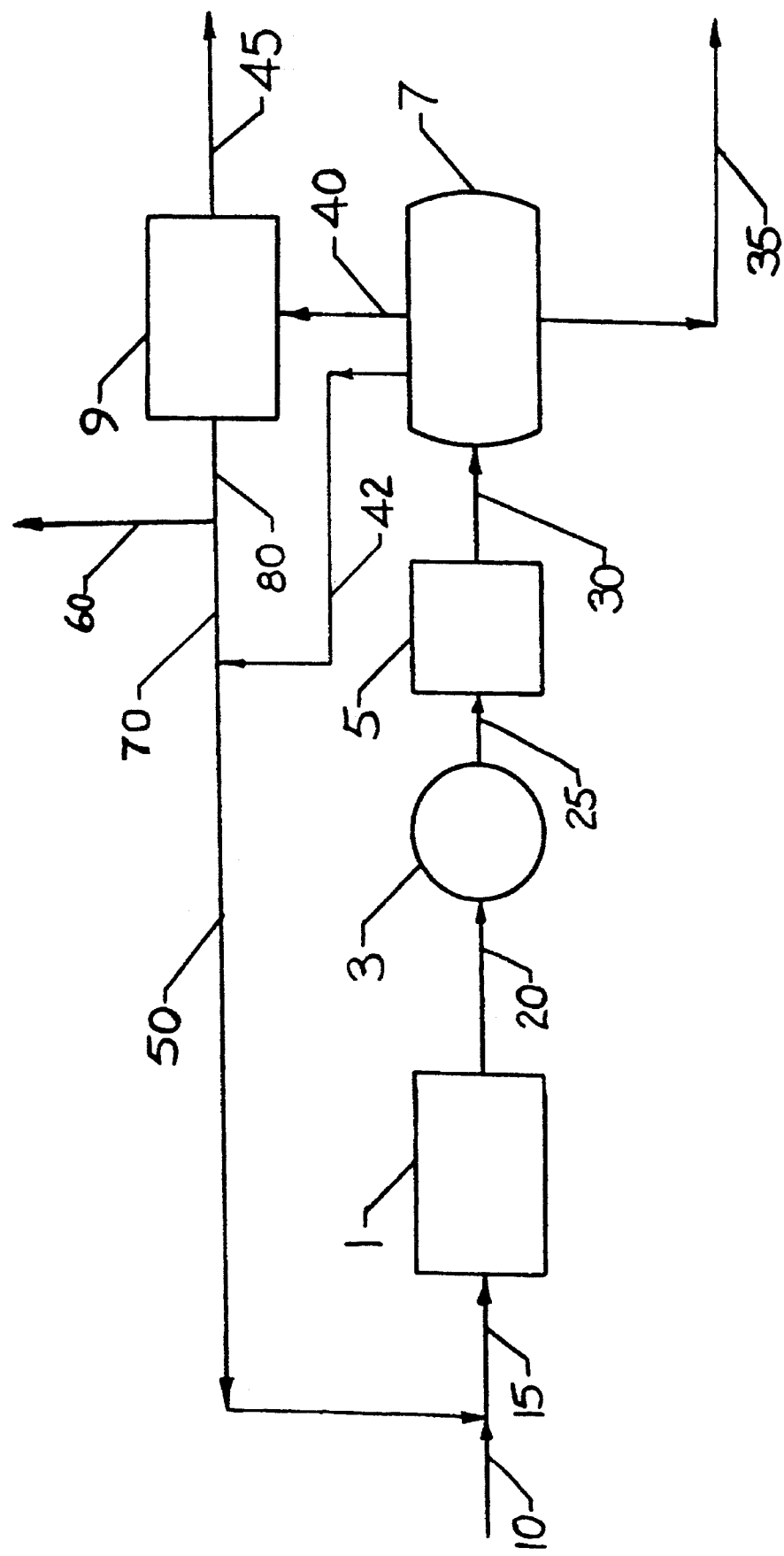

PROCESS FOR SEPARATING DEHYDROGENATION PRODUCTS

FIELD OF THE INVENTION

The present invention relates to a process for the catalytic dehydrogenation of $C_2+$ paraffinic hydrocarbons to produce low molecular weight, monoolefinic hydrocarbons. More particularly, the invention relates to a process which employs pressure swing adsorption and chilling for separating the products of the catalytic dehydrogenation reaction.

BACKGROUND OF THE INVENTION

Catalytic dehydrogenation as a commercially viable route to the production of olefinic hydrocarbons continues to grow in importance. $C_3$ and $C_4$ olefins have traditionally been recovered as by-products from either the steam cracking of natural gas, petroleum naphtha and gas oils in petrochemical plants, or from fluid catalytic cracking of petroleum gas oils in petroleum refineries. The production of the $C_3$ and $C_4$ olefins by these traditional methods has been largely non-selective, although some shifting of by-product yield can be obtained by changing feedstock composition or the cracking severity. However, the yields of specific $C_3$ or $C_4$ olefins, particularly monoolefins, are low and these changes may affect the yields of the primary products which may not be desirable.

When the desired production of a particular $C_3$ or $C_4$ olefin is required, a highly selective process is preferred. Catalytic dehydrogenation technology represents an economical method to produce propylene and butenes as primary products or in petrochemical complexes to alter the product distribution toward more profitable products. Products such as polymer grade propylene from propane, or normal and/or isobutenes from butane may be produced as commodity chemicals or converted into high value chemical products. For example, butanes can be converted into ethers such as methyl tertiary butyl ether (MTBE) in a complex comprising catalytic dehydrogenation, etherification and butane isomerization processes.

One example of a catalytic dehydrogenation process is taught in U.S. Pat. No. 4,381,417 to Vora et al. and is herein incorporated by reference. Vora et al. teach a process for the catalytic dehydrogenation of low molecular weight paraffinic hydrocarbons wherein the hydrogen-rich vapor streams resulting from each of the two vapor/liquid separations steps are recombined with the reactor effluent prior to compression, cooling and drying of the combined reactor effluent and hydrogen-rich stream. Because the light paraffins are relatively volatile, a more complicated separation scheme and a bulk condensation is normally required to effect the separation of the product olefins from the light by-products and hydrogen which are simultaneously produced in the process. It is therefore believed that U.S. Pat. No. 4,381,418 (Gewartowski et al.) is pertinent for its teaching of a catalytic dehydrogenation process for $C_2+$ normally gaseous paraffinic hydrocarbons and the recovery of the products of the reaction. U.S. Pat. Nos. 4,430,517 and 4,486,547 issued to Imai et al. and U.S. Pat. No. 4,469,811 issued to Lucien are believed pertinent for their teaching of catalysts and operating conditions which can be employed for the dehydrogenation of low molecular weight paraffins.

Pressure swing adsorption (PSA) provides an efficient and economical means for separating a multi-component gas stream containing at least two gases having different adsorption characteristics. The more-strongly adsorbable gas can be an impurity which is removed from the less-strongly adsorbable gas which is taken off as product; or, the more-strongly adsorbable gas can be the desired product, which is separated from the less-strongly adsorbable gas. For example, it may be desirable to remove carbon monoxide and light hydrocarbons from a hydrogen-containing feed stream to produce a purified (99+%) hydrogen stream for a hydrocracking or other catalytic process where these impurities could adversely affect the catalyst or the reaction. On the other hand, it may be desirable to recover more-strongly adsorbable gases, such as ethylene, from a feed to produce an ethylene-rich product.

In pressure swing adsorption, a multi-component gas is typically fed to at least one of a plurality of adsorption beds at an elevated pressure effective to adsorb at least one component, while at least one other component substantially passes through. At a defined time, feed to the adsorber is terminated and the bed is depressurized by one or more co-current to the direction of feed depressurization steps wherein pressure is reduced to a level which permits the separated, less-strongly adsorbed component or components remaining in the bed to be drawn off without significant removal of the more strongly adsorbed components. Then, the bed is depressurized by a countercurrent depressurization step wherein the pressure on the bed is further reduced by withdrawing desorbed gas countercurrently to the direction of feed. Finally, the bed is purged and repressurized.

U.S. Pat. Nos. 5,227,567 and 5,177,293 to Mitariten et at. teach processes for the separation and recovery of a product stream from a dehydrogenation reaction wherein a chiller system is employed to concentrate the olefin products and heavy hydrocarbons and a pressure swing adsorption unit is employed to separate a pure hydrogen stream from the heavy hydrocarbons. In U.S. Pat. No. 5,177,293, the desorbed hydrocarbons from the PSA unit are returned to the chiller and a portion of the pure hydrogen is returned to the dehydrogenation reactor. In U.S. Pat. No. 5,227,567, the desorbed hydrocarbons from the PSA unit are admixed with the reactor effluent from the dehydrogenation reactor, compressed, and charged to the chiller, while a potion of the hydrogen-rich gas from the PSA zone is returned to the dehydrogenation reactor. In both of these schemes, the capacity of the overall dehydrogenation system is limited by maximum vapor phase velocities within the dehydrogenation reactors. During the dehydrogenation reaction, by-products of the reaction tend to build up in the reactor/chiller system, thereby reducing the capacity of the overall dehydrogenation system and the efficiency of the separation of the dehydrogenation products.

Processes are sought which remove by-products of the reaction from the products of the reaction without allowing these by-products to build up in the recovery sections of the plant.

SUMMARY OF THE INVENTION

The invention provides a process for the production of olefinic hydrocarbons at essentially 100% recovery. The integration of a cold box unit and a pressure swing adsorption (PSA) unit in the manner of the present invention significantly improves the efficiency of the separation of the by-products of the dehydrogenation reaction by the removal of light paraffins such as methane and ethane from the system. Prior schemes recycled these light paraffins to chiller and heat exchange trains which in turn limited the capacity of the dehydrogenation reactor as the concentration of light paraffins in the recycle streams increased or built up in the system. Surprisingly, it was discovered that the capacity of the dehydrogenation reactor zone can be increased by approximately three moles of feedstream for every mole of light paraffin removed or rejected by the combination of the cold box and the PSA zone according to the instant invention. Thus, the capacity of $C_3$ to $C_5$ dehydrogenation schemes may be increased by up to 30% by the combination of the cold box and pressure swing adsorption zones according to the present invention.

In one embodiment the invention provides a process for the catalytic dehydrogenation of a feedstream comprising $C_2+$ paraffins. The feedstream is admixed with a recycle hydrogen stream to form a reactor feedstream. The reactor feedstream is passed to a dehydrogenation reactor to provide a reactor effluent comprising hydrogen, methane, and $C_2+$ olefins. The reactor effluent is compressed and dried to provide a dry reactor effluent stream. The dry reactor effluent stream is passed to a cold box to reduce the temperature of the dry reactor effluent to a liquefaction temperature in order to liquefy at least a portion of the dry reactor effluent and thereby provide a liquid product stream comprising $C_2+$ hydrocarbons and a light gas stream comprising hydrogen and methane. The light gas stream at adsorption conditions including an adsorption pressure is passed to a pressure swing adsorption zone containing an adsorbent selective for the adsorption of methane to provide the recycle hydrogen stream essentially free of methane and a net hydrogen stream enriched in methane. The net hydrogen stream is withdrawn whereby the buildup of methane in the recycle hydrogen is minimized.

BRIEF DESCRIPTION OF THE DRAWINGS

The drawing is a simplified process flow diagram of the process of the instant invention for the rejection of methane from a dehydrogenation process.

DETAILED DESCRIPTION OF THE INVENTION

Olefinic hydrocarbons such as propylene are one of the major building blocks of a large number of petrochemical products. Olefinic hydrocarbons such as butenes are also useful in petroleum refineries for the production of motor fuel blending components such as methyl tert. butyl ether (MTBE), tert. amylmethyl ether (TAME), ethyl tert. butyl ether (ETBE) and tert. butyl alcohol (TBA). The process of the present invention possesses utility in providing a more selective route than traditional methods for the production of these oleic hydrocarbons. Based upon the commercial desirability to produce olefinic hydrocarbons, there is a constant search for techniques to lower the cost of production of these olefinic. Surprisingly, it was discovered that by the rejection of methane from the product separation zone of a catalytic dehydrogenation process, significant capacity advantages can be realized. In particular, it was found that for each mole of methane removed from the hydrocarbon recycle, an additional mole of feedstock could be charged to the dehydrogenation reactor.

The term "dehydrogenatable hydrocarbons" as utilized herein is meant to refer to all classes of hydrocarbons containing saturated carbon bonds which have the potential for forming one or more unsaturated bonds through the process of dehydrogenation. The preferred dehydrogenatable hydrocarbons of the present invention consist of paraffinic type hydrocarbons. More specifically, the paraffin hydrocarbon charge stock of the present invention may contain from 2 carbon atoms to about 30 carbon atoms. Representative members of this class are: ethane, propane, butane, pentane, hexane, heptane, nonane, decane, undecane, dodecane, tridecane, tetradecane, pentadecane, hexadecane, heptadecane, octadecane, and mixtures thereof. A particularly important class of charge stocks include ethane, propane, butane, isobutane, pentane and mixtures thereof and which are readily prepared by the fractionation of relatively low boiling point hydrocarbon fractions.

Although various types of hydrocarbon feedstocks may be utilized in the process of the present invention, for purposes of specific exemplification, a feed stream comprising propane is described in detail.

The selected dehydrogenatable hydrocarbon feedstock is introduced into a dehydrogenation zone containing dehydrogenation catalyst and operated at dehydrogenation conditions to convert at least a portion of the dehydrogenatable hydrocarbons to produce a hydrocarbon stream comprising hydrogen, methane, dehydrogenated hydrocarbons and unconverted dehydrogenatable hydrocarbons. Preferably, the unconverted dehydrogenatable hydrocarbons are separated and recycled to the dehydrogenation zone together with the fresh feedstock.

The dehydrogenation catalyst may be employed in a fixed bed, fluidized bed, or a moving bed. Moreover, the dehydrogenation catalyst reaction zone may consist of multiple catalyst beds. In one such system, the catalyst is employed within an annular bed through which it is movable via gravity flow. In such a system, it is common practice to remove catalyst from the bottom of the reaction zone, regenerate it and then return it to the top of the reaction zone. Any suitable dehydrogenation catalyst may be used in the process of the present invention. Generally, the preferred catalyst comprises a platinum group metal component, an alkali metal component and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 $m^2/g$. The porous carrier material should be relatively refractory to the conditions utilized in the reaction zone and may be chosen from those carrier materials which have traditionally been utilized in dual function hydrocarbon conversion catalysts. A porous carrier material may therefore be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxide such as alumina, titanium dioxide, zirconium dioxides, magnesia, silica alum, alumina boria, crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/16".

The preferred dehydrogenation catalyst also contains a platinum group metal component. Of the platinum group metals, which include palladium, rhodium, ruthenium, osmium or iridium, the use of platinum is preferred. The platinum group component may exist within the final catalyst composite as a compound such as an oxide, sulfide, halide, oxysulfide, etc., of an elemental metal or in combination with one or more other ingredients of the catalyst. It is believed that the best results are obtained when substantially all platinum group components exist in the elemental state. The platinum group component generally comprises from about 0.01 to about 2 wt. % of the final catalytic composite, calculated on an elemental basis. It is preferred that the platinum content of the catalyst be between about 0.2 and 1 wt. %. The preferred platinum group component is platinum with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 3.5 wt. %, but is preferably between 0.2 and about 2.5 wt. % calculated on an elemental basis. This component may be added to the catalyst by the methods described above as a separate step or simultaneously with the solution of another component.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The dehydrogenation conditions which will be employed in the process of the present invention will, of course, vary depending on such factors as catalyst activity, feedstock, and desired conversion. A general range of conditions which may be employed for dehydrogenation of a light hydrocarbon include a temperature of from about 1022° F. (550° C.) to about 1472° F. (800° C.) a pressure of from about 0.01 to about 10 atmospheres absolute, a liquid hourly space velocity between about 0.1 and about 100 hr$^1$ and a hydrogen to hydrocarbon mole ratio from about 0.01:1 to about 40:1.

In accordance with the present invention, a hydrocarbon stream, for example, comprising propylene, propane, ethylene, ethane, methane, hydrogen and, in some cases, carbon dioxide, carbon monoxide and water is removed from the dehydrogenation reaction zone and is compressed to a pressure in the range from about 590 kPa (85 psia) to about 7 MPa (1015 psia). The resulting compressed hydrocarbon stream is cooled to a temperature in the range from about −117° C. (−180° F.) to about −29° C. (−20° F.) and introduced into a vapor-liquid separator. A liquid stream comprising at least a majority of the dehydrogenated hydrocarbons and the unconverted dehydrogenatable hydrocarbons contained in the effluent from the dehydrogenation zone is withdrawn from a vapor-liquid separator and recovered. A light gas stream comprising hydrogen, methane, and ethane is removed from the vapor-liquid separator and is passed to an adsorber bed containing adsorbent having adsorptive capacity for methane and heavier hydrocarbons at effective adsorption conditions. An effluent from the adsorber bed comprising a hydrogen-rich gaseous stream and having a reduced concentration of methane is recovered. At least a portion of the hydrogen-rich gaseous stream may be recycled to the dehydrogenation reaction zone, used to regenerate a spent adsorber bed, or used in some other useful manner.

Preferably the adsorber bed is a part of an integrated pressure swing adsorption (PSA) process whereby a continuous adsorber operation can be obtained while simultaneously regenerating a spent adsorber bed.

In accordance with the present invention, the pressure swing adsorption unit provides an efficient and economical means for separating a hydrogen-rich stream from methane and trace quantities of hydrocarbons. We contemplate that the PSA part of the present invention comprises a plurality of adsorption zones maintained at an elevated pressure effective to adsorb hydrocarbons while allowing the hydrogen to pass through the adsorber bed. At a defined time, the passing of the adsorber feed to one adsorber bed is discontinued and the adsorber bed is depressured by one or more co-current depressurization steps wherein the pressure is reduced to a defined level which permits additional hydrogen and light hydrocarbons components remaining in the adsorber bed to be withdrawn and utilized. Then the adsorber bed is depressurized by a countercurrent depressurization step wherein the pressure in the adsorber bed is further reduced by withdrawing desorbed hydrocarbons countercurrently to the direction of the feed. Finally, the adsorber bed is purged and repressured. A suitable purge gas is the co-current depressurization hydrogen-rich gas produced from another absorber vessel. The final stage of repressurization is with feed gas or light gases produced during the adsorption step.

The present invention can be performed using virtually any adsorbent material in the adsorber beds that have a preferential capacity for hydrocarbons as compared to hydrogen. Suitable adsorbents known in the an and commercially available include crystalline molecular sieves, activated carbons, activated clays, silica gels, activated aluminas and the like. The molecular sieves include, for example, the various forms of silicoaluminophosphates, and alumino-phosphates disclosed in U.S. Pat. Nos. 4,440,871; 4,310,440 and 4,567,027, hereby incorporated by reference as well as zeolitic molecular sieves.

Zeolitic molecular sieves in the calcined form may be represented by the general formula:

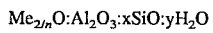

$Me_{2/n}O:Al_2O_3:xSiO:yH_2O$ where Me is a cation, x has a value from about 2 to infinity, n is the cation valence and y has a value of from about 2 to 10.

Typically well-known zeolites which may be used include chabazite, also referred to as Zeolite D, clinoptilolite, erionite faujasite, also referred to as Zeolite X and Zeolite Y, ferrierite, mordenite, Zeolite A, and Zeolite P. Other zeolites suitable for use according to the present invention are those having a high silica content, i.e., those having silica to alumina ratios greater than 10 and typically greater than 100. One such high silica zeolite is silicalite, as the term used herein includes both the silicapolymorph disclosed in U.S. Pat. No. 4,061,724 and also the F-silicalite disclosed in U.S. Pat. No. 4,073,865, hereby incorporated by reference.

Detailed descriptions of some of the above identified zeolites may be found in D. W. Breck, ZEOLITE MOLECULAR SIEVES, John Wiley and Sons, New York, 1974, hereby incorporated by reference. The patents referred to in the Background of the Invention contain further information concerning the various known adsorbents used for PSA operations and suitable for use in the practice of the invention.

It is often desirable when using crystalline molecular sieves that the molecular sieve be agglomerated with a binder in order to ensure that the adsorbent will have suitable physical properties. Although there are a variety of synthetic and naturally-occurring binder materials available such as metal oxides, clays, silicas, aluminas, silica-aluminas, silica-zirconias, silica-thorias, silica-berylias, silica-titanias, silica-alumina-thorias, silica-alumina-zirconias, mixtures thereof and the like, clay-type binders are preferred and examples which may be employed to agglomerate the molecular sieve without substantially altering the adsorptive properties of the zeolite are attapulgite, kaolin, volclay, sepiolite, polygorskite, kaolinite, bentonite, montmorillonite, illite and chlorite. The choice of a suitable binder and methods employed to agglomerate the molecular sieves are generally known to those skilled in the art and need not be further described herein.

The PSA cycle used in the present invention preferably includes the steps of adsorption, at least one co-current depressurization step, countercurrent desorption, purge and repressurization. Thus cycle steps are typically described with reference to their direction relative to the adsorption step. The cycle steps wherein the gas flow is in a concurrent direction to the adsorption step are known as "co-current" steps. Similarly, cycle steps wherein the gas flow is countercurrent to the adsorption step are known as "countercurrent" steps. During the adsorption step the feed stream is passed to the adsorber bed at an elevated adsorption pressure in order to cause the adsorption of the hydrocarbons and produce a hydrogen-rich gaseous stream. During the cocurrent depressurization steps the pressure in the depressurizing bed is released and the effluent obtained therefrom, which is rich in hydrogen, is passed in a countercurrent direction to another adsorber bed undergoing purge or repressurization. Typically, more than one co-current depressurization step is used wherein a first equalization step is performed after which a provide purge step is initiated wherein the adsorber bed is further co-currently depressured to provide a purge gas that is relatively impure with respect to the adsorbed component and thus is suitable for use as a purge gas. Optionally, a portion of hydrogen-rich adsorption effluent gas having a reduced concentration of hydrocarbons or an externally supplied gas can be used to supply the purge gas. Upon the completion of the co-current depressurization step, if employed, the adsorber bed is countercurrently depressurized to a desorption pressure in order to desorb the hydrocarbons. Upon completion of the desorption step, the adsorber bed is purged countercurrently with purge gas typically obtained from another bed. Finally, the adsorber bed is repressurized, first, typically with equalization gas from other adsorber beds and then with feed or product gas to adsorption pressure. Other additional steps known to those skilled in the art, such as, for example, a co-purge step wherein the adsorber bed is co-currently purged of the less strongly adsorbed components at an elevated pressure such as the adsorption pressure with a purge stream comprising hydrocarbons, can be employed.

The adsorber bed may suitably be operated at a pressure preferably in the range from about 276 kPa (40 psia) to about 3.4 MPa (500 psia), and more preferably in the range from about 500 kPa (75 psia) to about 2.7 MPa (390 psia). The operating temperature for the adsorber bed may be selected from the range from about −29° C. (−20° F.) to about 65° C. (150 ° F.). Additional operating conditions of the adsorber bed such as cycle times and rates of depressurization, for example, are not critical to the present invention and may readily be selected by a person skilled in the art.

DETAILED DESCRIPTION OF THE DRAWINGS

In the drawing, the process of the present invention is illustrated by means of a simplified flow diagram in which such details as pumps, instrumentation, heat-exchange and heat-recovery circuits, compressors, and similar hardware have been deleted as being non-essential to an understanding of the techniques involved. The use of such miscellaneous equipment is well within the purview of one skilled in the art.

With reference now to the drawing, a hydrocarbon feed stream comprising propane and trace quantifies of butane is introduced via conduit 10 and is admixed with a hereinafter described hydrogen-rich recycle stream which is carried via conduit 50 and the resulting admixture is introduced via conduit 15 into dehydrogenation reaction zone 1 to dehydrogenate at least a portion of the propane stream to provide a reactor effluent comprising hydrogen, methane, and dehydrogenated hydrocarbons, such as $C_3$–$C_4$ olefins. The reactor effluent is removed from the dehydrogenation reactor zone 1 via line 20 and passed to a compressor 3 where the reactor effluent is compressed to a pressure ranging from about 345 kPa (50 psia) to about 6.9 MPa (1000 psia), and preferably to pressure ranging from about 345 kPa to about 2.76 MPa (400 psia). The compressed reactor effluent is passed via line 25 to a dryer 5 thus reducing the water content of the compressed reactor effluent to less than about 5 ppm water to provide a dry reactor effluent. The dry reactor effluent is passed to a cold box 7 via a line 30 wherein the temperature of the dry reactor effluent is reduced to a temperature of between about −117° C. (−180° F.) and about −29° C. (−20° F.) at a pressure preferably ranging from about 345 kPa (50 psia) to about 6.9 MPa (1000 psia), and more preferably at a pressure ranging from about 345 kPa (50 psia) to about 2.76 MPa (400 psia). The cold box operates at cryogenic conditions and employs a Joule Thompson effect and refrigeration to separate hydrogen from the reactor effluent. The cold box contains heat exchange steps associated with the separation of the dry reactor effluent into a liquid product stream 35 comprising $C_2^+$ hydrocarbons and a light gas stream 40 comprising hydrogen. Also produced in the cold box as a result of associated multiple cooling and flashing steps is a light recycle stream 42 comprising hydrogen and methane. The liquid product stream 35 comprising $C_2^+$ hydrocarbons and the light gas stream 40 comprising hydrogen and methane are withdrawn from the cold box 7. A light recycle stream 42 is withdrawn from the cold box 7 and is combined with a portion of adsorption effluent in line 70 and is passed by line 50 to be recycled to the dehydrogenation reactor zone 1. The light gas stream 40 at an adsorption pressure ranging from 275 kPa (40 psia) to about 2.7 MPa (390 psia) is withdrawn in line 40 and passed to a pressure swing adsorption unit 9. The pressure swing adsorption unit 9 contains an adsorbent selected from the group consisting of alumina, silica gel, activated carbon, molecular sieves, and mixtures thereof which is selective for the adsorption of methane over hydrogen to provide an adsorber effluent stream 80 and a desorption effluent in stream 45. The adsorber effluent stream 80 comprises hydrogen and is essentially free of methane. Preferably the adsorber effluent stream comprises between 97 and 99 mol % hydrogen, more preferably the adsorber effluent comprises between 99 and 99.9 mol % hydrogen and most preferably the adsorber effluent comprises at least 99.9 mol % hydrogen. At least a portion of the adsorption effluent is returned in lines 70 and 50 as the recycle hydrogen stream to be admixed with the feedstream in line 10. The desorption effluent is withdrawn from the pressure swing adsorption zone as a net hydrogen stream in line 45. The net hydrogen stream 45 may be optionally compressed to a higher pressure in a net gas compressor (not shown). The net hydrogen stream comprises methane and the removal of the net hydrogen stream which further comprises about 40 mol % hydrogen to about 70 mol % hydrogen, removes methane from the dehydrogenation reaction zone and separation zone whereby the build-up of methane in the recycle hydrogen to the dehydrogenation reaction zone or the cold box zone is minimized. At least a portion of the recycle hydrogen stream in line 60 is withdrawn as a hydrogen product stream for use in other hydrocarbon conversion processes.

Surprisingly, it was discovered that the removal of methane and some ethane from the recycle hydrogen according to the present invention had a significant impact on the capacity of the dehydrogenation reaction zone. For a $C_3$ dehydrogenation unit, which originally contained about 23% methane in the recycle hydrogen, the addition of the cold box and PSA zones, as illustrated in FIG. 1, permitted an additional 30% more feed to be processed in the dehydrogenation reaction zone. For a $C_4$ dehydrogenation scheme which generally produces less methane in the reaction zone and contained about 11.7% methane in the recycle hydrogen stream, the benefits of applying the present invention permitted about a 9.2% increase in the capacity of the dehydrogenation zone. The production of light paraffinic gases such as methane and ethane is largely a function of the severity of the dehydrogenation reaction. As the severity of the reaction is increased and more light paraffinic gases are produced, the benefit of the present invention will increase accordingly. The expected increase in dehydrogenation reaction capacity will also vary with the composition of the feed being dehydrogenated. For a $C_3$ dehydrogenation scheme, the expected percentage capacity increase of the reaction zone will range from about 20 to about 35%. For a $C_4$ dehydrogenation scheme, the expected capacity increase will range from about 5 to about 15%, and for a $C_5$ dehydrogenation scheme, the expected capacity increase in the reaction zone will be less than about 5%.

EXAMPLES

The following examples are provided to illustrate the process of the present invention and are not intended to limit the scope of the claims that follow. The examples are based on process engineering design calculations and reaction and adsorption relationships based on commercial data for the operation of the dehydrogenation reaction zone and the pressure swing adsorption zone for the separation of hydrogen from light hydrocarbons.

EXAMPLE I

With reference to Table 1, a conventional separation scheme with a cold box was employed in a system for the dehydrogenation of a $C_3$ hydrocarbon stream to produce a $C_3$ olefin-product. The hydrocarbon feed stream was combined with a recycle hydrogen stream comprising hydrogen and methane and the combined stream was passed to a dehydrogenation reaction zone. The reactor effluent from the dehydrogenation reaction zone was compressed to a pressure of about 1.03 MPa (150 psia), dried to remove water, and passed to a cold box. In the cold box, the dried reactor effluent was reduced to a temperature of about −115° C. at a pressure of about 414 kPa (60 psia) and flashed to provide a hydrocarbon product and a recycle hydrogen stream. A light recycle stream comprising hydrogen and methane produced in the cold box was recycled directly to the dehydrogenation reactor zone by combining the light recycle stream with the recycle hydrogen. The C2 hydrocarbon values shown in the table include ethane, ethylene and trace quantities of heavier hydrocarbons. A portion of the recycle hydrogen stream was withdrawn as a net hydrogen product. As shown in Table 1, the hydrocarbon feed rate was about 3086 moles/hour and the hydrogen recycle rate was about 4432 moles/hour which resulted in a cold box feed rate of dried reactor effluent of 8980 moles/hour. The recycle hydrogen purity was about 75.5 mol % hydrogen and the amount of net hydrogen product withdrawn at this purity was 931 moles/hour. An olefin product was produced at a rate of 3156 moles/hour.

EXAMPLE II

With reference to the Figure and Table 2, a process scheme for dehydrogenation of a $C_3$ paraffin based on the present invention employing a cold box in combination with a pressure swing adsorption zone was evaluated for the fixed cold box capacity of 8980 moles/hour of Example I. The dried reactor effluent was reduced to a temperature of about −112° C. in a cold box at a pressure of about 448 kPa (65 psia) in the cold box and was flashed to provide a $C_3$ olefin product and a light gas stream comprising hydrogen and methane. A light recycle stream was produced in the cold box as a result of a series of multiple flashing steps. This light recycle stream was returned to the dehydrogenation reactor. The $C_2^+$ hydrocarbon value includes ethane, ethylene, and trace amounts of heavier hydrocarbons. The light gas stream was passed to a PSA zone at an adsorption pressure of about 1.24 MPa (180 psia) and an adsorption temperature of about 41° C. to provide a recycle hydrogen stream with a purity of about 99.9 mol % hydrogen and a net hydrogen product at a desorption pressure of about 110 kPa (16 psia) with a purity of about 71 mol % hydrogen. A small compressor optionally may be employed to increase the pressure of the light gas stream prior to being passed to the PSA zone to improve recovery in the PSA zone. The net hydrogen product was recompressed to a pressure of about 655 kPa (98 psia). Surprisingly, it was discovered that the addition of the PSA zone to the cold box scheme of Example I permitted the hydrocarbon feed rate to be increased from 3086 to 4013 moles/hr at the same cold box capacity. This represented a 30 percent increase in feed capacity and resulted in the production of about 27.5 percent more olefin product. In addition, the net hydrogen produced in the amount of 1285 moles/hr at a purity of about 71 mol % represented an increase of about 38% over the net hydrogen produced in Example I. By the addition of the pressure swing adsorption zone in combination with the cold box zone according the present invention, the feed rate to the overall dehydrogenation system could be increased about 30% in capacity without any further investment in the dehydrogenation reaction zone. The benefit of increasing the dehydrogenation zone capacity outweighs the relatively minor losses (<0.2 mol %) of dehydrogenation zone product in the net hydrogen produced. Surprisingly, for an incremental increase in the removal of methane of 120 moles/hr in the net hydrogen product, the build-up of methane in the recycle hydrogen was essentially eliminated, resulting in a 2.75 fold increase in the incremental molar feed rate of 927 moles/hr to the dehydrogenation reactor.

We claim:

1. A process for the catalytic dehydrogenation of a feedstream comprising $C_2+$ paraffins said process comprising the following steps:

a) admixing said feedstream with a recycle hydrogen stream to form a reactor feedstream and passing said reactor feed stream to a dehydrogenation reactor to produce a reactor effluent stream comprising hydrogen, methane, and $C_2+$ olefins;

b) compressing and drying said reactor effluent stream to produce a dry reactor effluent stream and passing said dry reactor effluent stream to a cold box to reduce the temperature of the dry reactor effluent stream to a liquefaction temperature in order to liquefy at least a portion of said dry reactor effluent stream to provide a liquid product stream comprising $C_2+$ hydrocarbons and a light gas stream comprising hydrogen and methane; and c) passing the light gas stream at an adsorption pressure to a pressure swing adsorption zone containing an adsorbent selective for the adsorption of methane to produce the recycle hydrogen stream as an adsorption effluent being essentially free of methane and a net

TABLE 1

CONVENTIONAL DEHYDROGENATION WITH COLD BOX

| STREAM: | HYDROCARBON FEED | COLD BOX FEED | OLEFIN PRODUCT | RECYCLE HYDROGEN | NET HYDROGEN | LIGHT RECYCLE |
|---|---|---|---|---|---|---|
| FLOW RATES, MOLES/HR | | | | | | |
| HYDROGEN | <1 | 4288 | <1 | 3341 | 703 | 244 |
| METHANE | <1 | 1580 | 109 | 1051 | 221 | 199 |
| $C_2$ HYDROCARBON | 30 | 310 | 259 | 34 | 6 | 11 |
| $C_3$ HYDROCARBON | 3056 | 2802 | 2788 | 6 | 1 | 7 |
| TOTAL | 3086 | 8980 | 3156 | 4432 | 931 | 461 |
| CONDITIONS: | | | | | | |
| TEMPERATUPE, °C. | 49 | 41 | 38 | −115 | 38 | 38 |
| PRESSURE, MPa | 2.14 | 1.03 | 4.14 | 0.41 | 0.65 | 0.41 |

TABLE 2

DEHYDROGENATION COMBINED WITH COLD BOX AND PSA

| STREAM: | HYDROCARBON FEED | COLD BOX FEED | OLEFIN PRODUCT | RECYCLE HYDROGEN | NET HYDROGEN | LIGHT RECYCLE |
|---|---|---|---|---|---|---|
| FLOW RATES, MOLES/HR | | | | | | |
| HYDROGEN | <1 | 4385 | <1 | 3213 | 912 | 260 |
| METHANE | <1 | 603 | 90 | 3 | 341 | 169 |
| $C_2$ HYDROCARBON | 40 | 362 | 319 | — | 23 | 20 |
| $C_3$ HYDROCARBON | 3973 | 3630 | 3615 | <1 | 9 | 6 |
| TOTAL | 4013 | 8980 | 4024 | 3217 | 1285 | 445 |
| PROCESS CONDITIONS: | | | | | | |
| TEMPURATURE, °C. | 120 | 41 | 41 | −112 | 41 | 41 |
| PRESSURE, MPa | 2.14 | 1.03 | 4.14 | 0.45 | .65 | 0.4 |
| PSA CONDITIONS: | | | | | | |
| ADSORPTION, TEMPERATURE, °C. | 41 | | | | | |
| PRESSURE, MPa | 1.24 | | | | | |
| DESORPTION, TEMPERATURE, °C. | 41 | | | | | |
| PRESSURE, TEMPERATURE, °C. | 110* | | | | | |

*Net $H_2$ recompressed to 0.655 MPa hydrogen stream as a desorption effluent being enriched in methane, and withdrawing said net hydrogen stream, whereby a buildup of methane in the recycle hydrogen stream is minimized.

2. The process of claim 1 wherein the $C_2+$ paraffins are selected from the group consisting of $C_3$, $C_4$, $C_5$ paraffins and mixtures thereof.

3. The process of claim 1 wherein the recycle hydrogen stream comprises between 97 and about 99 mol % hydrogen.

4. The process of claim 1 wherein the recycle hydrogen stream comprises between about 99 and about 99.99 mol % hydrogen.

5. The process of claim 1 wherein the recycle hydrogen stream comprises at least 99.9 mol % hydrogen.

6. The process of claim 1 wherein said liquefaction temperature ranges from about $-112°$ C. ($-180°$ F.) to about $-29°$ C. ($-20°$ F.).

7. The process of claim 1 wherein said reactor effluent stream is compressed to a pressure ranging from about 345 kPa (50 psia) to about 2.76 MPa (400 psia).

8. The process of claim 1 wherein said adsorption pressure ranges from about 276 kPa (40 psia) to about 3.4 MPa (500 psia).

9. The process of claim 1 wherein said adsorption pressure ranges from about 500 kPa (70 psia) to about 2.7 MPa (390 psia).

10. The process of claim 1 wherein the adsorbent selective for the adsorption of methane is selected from the group consisting of alumina, silica gel, activated carbon, molecular sieves, and mixtures thereof.

11. A process for the catalytic dehydrogenation of a feedstream comprising $C_3$ paraffins said process comprising the following steps:

a) admixing said feedstream with a recycle hydrogen stream to form a reactor feedstream and passing the reactor feedstream to a dehydrogenation reactor to produce a reactor effluent stream comprising hydrogen, methane, and $C_3$ olefins;

b) compressing and drying said reactor effluent stream to produce a dry reactor effluent stream and passing the dry reactor effluent stream to a cold box to reduce the temperature of the dry reactor effluent to a liquefication temperature in order to liquefy at least a portion of said dry reactor effluent stream to produce a liquid stream comprising $C_2+$ hydrocarbons and a light gas stream comprising hydrogen and methane;

c) passing the light gas stream at an adsorption pressure to a pressure swing adsorption zone containing an adsorbent selective for the adsorption of methane to produce the recycle hydrogen stream as the adsorption effluent being essentially free of methane and a net hydrogen stream as the desorption effluent being enriched in methane, and withdrawing the net hydrogen stream, whereby a build-up of methane in the recycle hydrogen stream is minimized;

d) withdrawing at least a portion of the recycle hydrogen stream as a hydrogen product stream.

12. The process of claim 11, wherein the feedstream comprises $C_4$ paraffins.

* * * * *